United States Patent [19]

Snyder

[11] 4,248,853
[45] Feb. 3, 1981

[54] ASSAY METHOD AND KIT

[75] Inventor: Solomon H. Snyder, 2300 W. Rogers Ave., Baltimore, Md. 21209

[73] Assignee: Solomon Halbert Snyder, Baltimore, Md.

[21] Appl. No.: 940,712

[22] Filed: Sep. 8, 1978

[51] Int. Cl.$^3$ ..................... G01N 33/48; A61K 43/00; G01T 1/00

[52] U.S. Cl. ..................................... 424/1; 23/230 B; 422/61; 424/12

[58] Field of Search ................... 424/1, 12; 23/230 B; 422/61

[56] References Cited

U.S. PATENT DOCUMENTS

| | | | |
|---|---|---|---|
| 4,026,879 | 5/1977 | Spector | 424/1 |
| 4,070,492 | 1/1978 | Spector | 424/1 |

OTHER PUBLICATIONS

Innis et al., Life Sciences, vol. 23 (1978), pp. 2031-2038.
Snyder et al., Nature, vol. 270 (Nov. 1977) pp. 261-263.
Nahorski et al., Eur. J. Pharma., 52, (1979), pp. 393-396.
Bilezikian et al., Clin. Pharmacol. Ther., vol. 26, No. 2 (1979), 173-180.

*Primary Examiner*—Benjamin R. Padgett
*Assistant Examiner*—Christine M. Nucker
*Attorney, Agent, or Firm*—Donald Brown

[57] ABSTRACT

Method and materials for determining levels of β-adrenergic blocking drugs in body fluid, the method including the step of measuring inhibition of the binding of β-adrenergic receptor binder to β-adrenergic receptor material caused by β-adrenergic blocking drug present in the body fluid.

24 Claims, 1 Drawing Figure

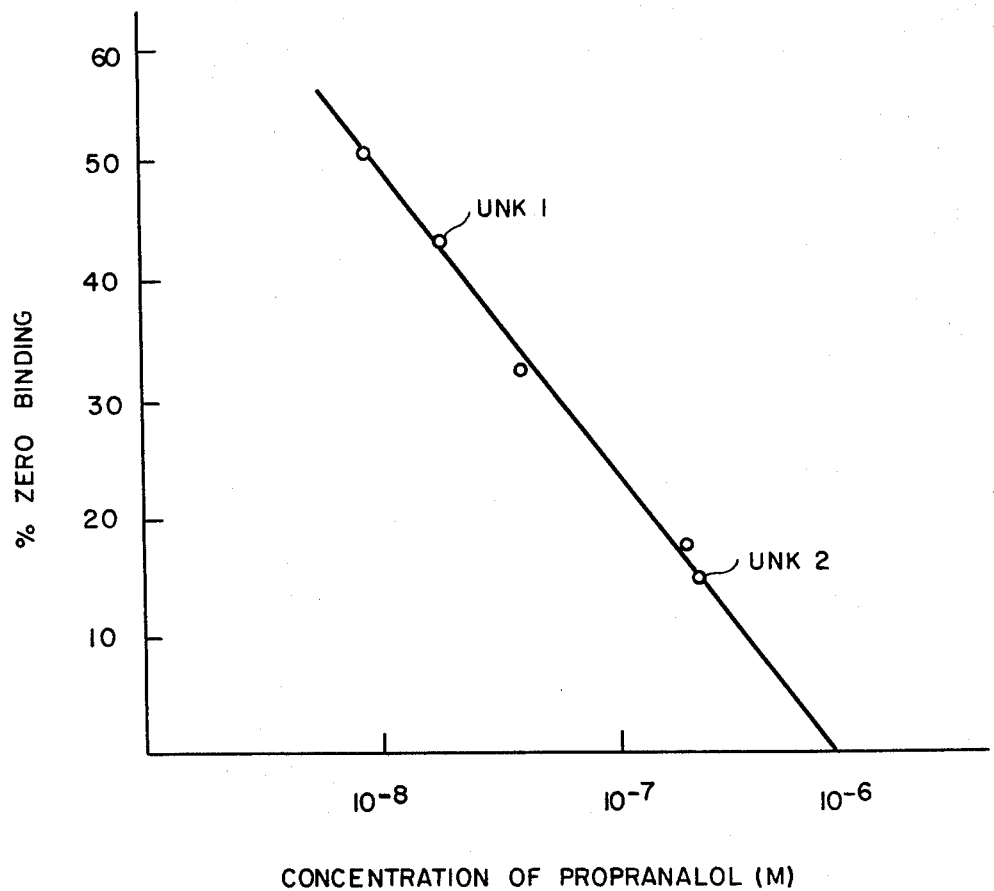

ASSAY METHOD AND KIT

BACKGROUND OF THE DISCLOSURE

Drugs which can block β-adrenergic receptors are among the most valuable agents used presently in clinical medicine. In the United States the major drug employed clinically is propranolol, while numerous other agents are available commerically in Europe and probably will be used in the United States within the next few years. These drugs are used extensively throughout the world for the treatment of hypertension and angina pectoris. Dosage requirements can vary considerably among different patients. In part the variable dose requirement is related to differences in absorption and metabolism of the drug among individuals. Attaining the optimal dose is important in securing maximal therapeutic benefit and in avoiding potentially serious side effects of these drugs such as abnormalities in cardiac rhythm and blood pressure. It is generally felt that a simple and sensitive technique to measure these drugs in blood and other body tissues would facilitate the selection of optimal doses.

Detecting β-adrenergic blocking drug levels in body fluids ideally should employ a technique which can be used with all of the agents. Moreover, it has been established with propranolol that a metabolite of the drug 4-hydroxypropranolol has therapeutic activity so that an ideal method should be able to measure pharmacologically active but not inactive metabolites in addition to the parent drug.

Presently available techniques include gas-liquid chromatography, fluorimetric procedures as well as radio-immunoassays. None of these have attained routine clinical use because of various technical problems. Most of these techniques are applicable for individual drugs rather than for the whole class of β-blocking agents. Also such prior art methods do not specifically detect active metabolites.

β-adrenergic blocking drugs were developed on the basis of their ability to antagonize the effects of adrenergic stimulating substances such as the natural neurotransmitter, norepinephrine or its analogue, isoproterenol, which has a uniquely high potency in stimulating β-adrenergic receptors. In recent years it has been possible to label β-adrenergic receptors in a variety of tissues using radio-active β-blocking drugs (binder) such as $^3$H-dihydroalprenolol and $^{125}$I-hydroxybenzylpindolol. See the publications Lefkowitz et al, Biochem. Biophys. Res. Commun. 60:703-709, 1974; Aurbach et al, Science, 186:1223-1224, 1974. Neither of these publications nor any of several publications appearing in the succeeding years describing the binding of these and other radioactive drugs to the β-receptor have disclosed anything beyond the fact that β-adrenergic receptors can be measured with various radioactive forms of β-blocking drugs and that β-blocking drugs compete with the binding of these radioactive agents for the receptor. Moreover, the information contained in these above-mentioned publications does not provide a tool for measuring amounts of β-blocking drugs in body fluids of human patients, because a number of needed elements, all of which were yet to be discovered, had to be discovered to exist for a successful assay for levels of β-blocking drugs. For a successful assay for β-blocking drug levels it was necessary to discover the nonspecific effects of body fluids on the binding properties of the β-receptors and discover means of reducing or abolishing them. It was also necessary to discover that β-blocking drugs added to body fluids could be recovered in a form that would still interact with the β-adrenergic receptors. It was also necessary to show that in the presence of body fluids increasing amounts of β-blocking drugs would in a predictable fashion produce progressively greater blockade of β-receptors. Only after making a series of discoveries as disclosed herein which reduced nonspecific effects of body fluids on the β-receptors, permitted recovery of added β-blocking drugs and resulted in reproducible augmentations in receptor blockade with increasing amounts of β-blocking drugs in body fluids was it possible to measure β-blocking drugs in body fluids with this invention.

BRIEF DESCRIPTION OF THE DISCLOSURE

The present invention is directed to a new technique which permits rapid determination of the concentration of β-adrenergic blocking drugs in patients. The making of this determination was important in order to obtain the desired medicinal effect of these drugs. While the desirable concentration of β-adrenergic blocking drug in the patient's blood or other bodily fluids is known, it has been found that the uptake of these drugs by most patients is variable so that one has no assurance that a certain dose of β-adrenergic blocking drug administered to the patient will produce the desired concentration in the blood. The prior art techniques for measuring the concentrations of β-blocking drugs, as mentioned previously, are not applicable to all available β-adrenergic blocking drugs and do not detect active but not inactive metabolites. Accordingly, a new and improved technique that could easily and rapidly be used was needed to insure that patients were being properly dosed to achieve beneficial effects without causing harmful side effects.

The present invention provides such a technique and is based on the fact that β-adrenergic blocking drugs will successfully compete with the binding of radioactive β-blocking drugs to β-adrenergic receptors in such a manner that an accurate determination of β-adrenergic blocking drug concentration can readily be determined.

The present invention is also based in part upon the discovery that once the competition of radioactive β-adrenergic blocking drug to the β-adrenergic receptor has proceeded for the desired time, labeled drug and receptor can be successfully separated from free drug and receptor and bodily fluids without destroying the accuracy of the concentration measurement to be made.

After the separation, the level of radioactive β-blocking drug may be measured in a conventional radioactive measurement device, e.g. scintillation counter or gamma counter depending on the radionuclide of the radioactive β-adrenergic blocking drug and compared with standard curves to determine the concentration of the β-adrenergic blocking drug in the patient.

Thus, there is described herein a method for measuring levels of β-blocking drugs in patients based on the ability of these drugs to compete with the binding of radioactive β-blocking drugs (ligands) including β-adrenergic antagonists or agonists to β-adrenergic receptors in β-adrenergic receptor containing material.

In this procedure increasing amounts of β-adrenergic blocking drugs or active metabolites thereof decrease the binding of the radioactive labeled binder to the β-adrenergic receptor material. The biological fluid sample may be assayed without separation of the β-adrenergic blocking drug therefrom, e.g. blood serum or blood plasma may be directly assayed to determine the β-blocking drug levels.

Suitable β-adrenergic receptor material is obtained from animal tissues enriched in these receptors such as the brain, heart, lung and blood cells. Suitable receptor material is obtained from humans or from animal species such as bovine, rodent (rat) or birds.

The β-adrenergic receptor material may be used as such or fractionated in a conventional manner to obtain fractions enriched in receptor-containing membranes and may be washed or unwashed.

The β-adrenergic receptor material may preferably be sold as a conventional freeze-dried preparation in a test tube, e.g. coupled to the interior of a test tube so that the binder and drug may be easily added to it.

As the radioactive β-adrenergic receptor binder, radioactive labeled compounds such as $^3$H-dihydroalprenolol, $^{125}$I-hydroxybenzylpindolol, $^3$H-epinephrine or any other analogues or norepinephrine or of β-adrenergic blocking drugs having the β-adrenergic receptor binding properties exhibited by these compounds may be used.

In principal, these compounds are conventionally labeled in the manner well known in the prior art with any radio-nuclide. A listing of the radionuclides which are now conventionally in use in reagents and which may be used in this invention are listed in the index of radionuclides found on page 81 of the 1978 edition of the Catalogue of the New England Nuclear Corporation, Boston, Massachusetts, U.S.A. (New England Nuclear, 1977). Among radionuclides which are preferred in this invention the following may be mentioned: hydrogen-3 (tritium) and the radio isotopes of iodine ($^{123}$I, $^{124}$I, $^{125}$I, $^{126}$I, $^{128}$I, $^{130}$I and $^{132}$I) with $^{125}$I and $^{131}$I being preferred from considerations of availability, half life and specific activity and the ability of radioactive iodine compounds to be readily labeled using a conventional gamma counter usually available in hospitals and sold by Packard Instruments or others.

In a typical experiment the membranes (β-adrenergic receptor material) can be incubated at various temperatures for various periods of time with appropriate ligand (β-adrenergic receptor binder). Typically $^3$H-dihydroalprenolol of high specific radioactivity purchased from New England Nuclear of Boston, Massachusetts is incubated with rat brain membranes in a buffer solution preferably at a pH of 7.7 at a temperature of 37° for 30 min. and then filtered undre vacuum through Whatman GF/B filters with two 5 ml. rinses of cold buffer. The filters can be counted in liquid scintillation counters, e.g. Packard Instrument scintillation spectrometer model 3385. Counting may also be accomplished using a gamma counter.

Specific binding to the β-adrenergic receptor is determined as the excess over blanks taken in the presence of 10 μM norepinephrine or 0.1 μM propranolol though blank values can be obtained using a variety of other agents that bind to the β-adrenergic receptor. The ligand can be any β-adrenergic agonist or antagonist or mixed agonist-antagonist labeled with radioactivity.

Biological fluid samples, e.g. urine, blood plasma, blood serum, etc., supposedly containing β-adrenergic blocking drugs are added to this assay. The biological samples can be added without any purification or may be subjected to purification procedures. Purification or concentration of the biological fluid containing the β-blocking drugs can employ any of numerous chemical techniques including solvent extraction, column chromatography, adsorption onto specially treated fibers or other chemical substance or by any other chemical procedure which may help purify the β-blocking drug or concentrate. The amount of β-adrenergic blocking drug is quantified by the extent to which it decreases binding of the labeled ligand to the β-adrenergic receptor. The values can be quantified in any convenient units. The incubation mixture for the receptor binding can include any of numerous additives to facilitate binding or to protect the drugs or labeled ligands. The duration of the incubation and its temperature can vary and involve any convenient period, though it is usually best to conduct the incubation to equilibrium, e.g. suitable time for incubation could be anywhere from two min. to 4 hrs. with 30 min. being preferred. Receptor bound ligand can be trapped by filtration, centrifugation or any other known techniques which separate bound from unbound ligand.

It should also be understood that other suitable trapping technique may also be used so long as it will permit the retention of the large sized β-adrenergic receptor material having bound radioactive binder and β-adrenergic blocking drug while being able to separate the unbound radioactive binder (ligand) and free β-adrenergic blocking drug. Other examples of suitable filter material include Millipore filters of various sizes, e.g. 0.6 micron diameter holes.

Preferably the β-adrenergic receptor material is buffered by a buffering solution such as Tris-HCl buffer sold by Sigma Labs, St. Louis, Missouri, having a pH of 7.7. Other suitable buffering solutions include sodium phosphate buffer, glycine buffer and Hepes buffer and others which will provide the preferred pH (6–9) in the mixture to permit rapid binding of the radioactive labeled binder to the β-adrenergic receptor material.

Thus this invention provides a new and improved method for determining concentration in humans of β-adrenergic blocking drugs such as propranolol, practolol, pindolol, alprenolol, sotalol, butoxamine, and others which are known in the art as competitors at β-adrenergic receptors.

In particular, the method is easily practiced by preparing a mixture of radioactive binder, body fluid, e.g. blood serum, blood plasma or urine and β-adrenergic receptor material, measuring the radioactivity (counts) of the binder attached to the β-adrenergic receptor material preferably after separating unbound materials, (e.g. blood serum or plasma, binder, drug if present, etc.) from the β-adrenergic receptor material and then deriving the concentration of the β-adrenergic blocking drug from a standard curve which indicates the concentration of β-blocking drug versus inhibition of the radioactive binder binding to the β-adrenergic receptor material caused by the β-adrenergic blocking drug in the blood serum or plasma.

It has been discovered that the concentrations of body fluids such as blood plasma or blood serum in the assay are most preferably no greater than about 10% of the total assay volume of ingredients in the test tube. Concentrations of plasma or serum in excess of about 10% inhibit markedly binding of $^3$H-ligands to the β-adrenergic receptor even without any drug present. Optimally the concentration values should be less than 10%. Concentrations in excess of 10% may affect the validity of the assay test results. In this method the amount of body fluid is preferably greater than one microliter to assure consistently good results. As used herein the total assay volume ingredients means the sum of ingredients in the test tube and the like prior to washing and adding scintillation fluid.

In addition, this invention provides a new composition of matter concerning radioactive binder, β-adrenergic blocking drug and β-adrenergic receptor material and blood serum or plasma and a kit comprising the ingredients for performing the technique described herein.

BRIEF DESCRIPTION OF THE DRAWINGS

The drawing herein is a graph showing percent zero binding vs propranolol in molar concentration reported in the example.

The following example illustrates measurement of blood serum propranalol levels:

MATERIALS

I. β-adrenergic receptor

Cerebellar membranes were used as a source for β-adrenergic receptors. Three rats were decapitated. Their cerebellum, which had a combined weight of 0.72 g, was immediately dissected and homogenized in 10 ml. of ice-cold 50 μM Tris.HCl buffer, pH 7.7 with a Brinkman polytron (setting 3.7) for two minutes. Twenty milliliters of the Tris buffer was then added to the homogenate and the homogenate was centrifuged at 4° C. for 10 minutes at 40,000×g in a Sorval RC5 centrifuge. The pellet was homogenized in 10 ml. of the ice-cold Tris buffer with a polytron as previously described. Twenty milliliters of the ice-cold Tris buffer were added and the homogenized pellet was centrifuged at 40,000×g for 10 minutes. The pellet was again homogenized as previously described in 10 ml. of ice-cold 50 μM Tris HCl, pH 7.7 and adjusted to a final volume of 30 ml. by adding 20 ml. of ice-cold 50 μM Tris HCl pH 7.7.

II. Propranolol standards

Six propranolol standards were prepared by dissolving varying concentrations of d,l-propranolol in pooled human serum as follows:
A. $10^{-4}$ M propranolol in human serum.
B. Human serum with no added propranolol.
C. $10^{-6}$ M propranolol in human serum.
D. $2\times10^{-7}$ M propranolol in human serum.
E. $4\times10^{-8}$ M propranolol in human serum.
F. $8\times10^{-9}$ M propranolol in human serum.

As used herein human serum means human blood serum.

III. Unknown

Patient's serum or d,l-propranolol dissolved in human serum.

IV. Labeled ligand l[propyl-2,3-$^3$H]dihydroalprenalol (30 Ci/m mol), obtained from the Radiochemical Centre, Amersham, was diluted in 50 μM Tris HCl pH 7.7 to give 10,000 CPM per 20 μl.

V. Assay procedure

The assay is performed in 12×75 mm glass test tubes. Standard and unknown samples are assayed in triplicate. To each tube the following additions are made in order while the tubes are kept on ice: Twenty microliters of propranolol standard or 20 μl of unknown, twenty microliters of labeled ligand, one milliliter of μ-adrenergic receptor cerebellar membranes. The tubes are then mixed with a vortex mixer and incubated at room temperature for 30 minutes. After this incubation the contents of tubes are each rapidly filtered with suction through Whatman GF/B glass fiber filters which have been placed in a filter manifold. The filters are rapidly washed twice with 5 ml. of ice-cold 50 μM Tris HCl pH 7.7. The filters are then placed in 12 ml. of Aquasol in 20 ml. liquid scintillation vials. After 16 hours the filters are counted for 2 minutes in a liquid scintillation counter using a $^3$H window setting (Packard Spectrometer).

VI. Calculation of results

The average counts per minute for each set of triplicates is obtained. The average minus background counts per minute is obtained by subtracting the average counts per minute for standard A from the average counts per minute for each other set of standards and unknowns. The % zero binding is obtained by dividing the average minus the background counts per minute for each set of standards and unknowns by the average minus the background counts per minute for standard B and multiplying the result by 100. The % zero binding for the standards are then plotted against the log 10 of the concentration of propranolol in each standard. The log 10 of concentration of propranolol in the unknown is then determined by reading of the % zero binding for each unknown. The anti-logarithm then will give the concentration of propranolol in the unknown sample.

Example

| Sample | Ave. CPM | Ave-BKG CPM | % Zero binding |
|---|---|---|---|
| Standard A | 789 | | |
| Standard B | 1574 | 785 | |
| Standard C | 619 | <0 | <0 |
| Standard D | 937 | 148 | 18.9 |
| Standard E | 1047 | 258 | 32.9 |
| Standard F | 1186 | 397 | 50.6 |
| Unk1($2\times10^{-7}$M proran) | 911 | 122 | 15.5 |
| Unk2($10^{-8}$M proran) | 1128 | 339 | 43.2 |

See the drawing (graph) which illustrates a plot of the data in the example and shows the concentration of propranolol of the unknown 1 and 2 in terms of molar concentration.

I claim:

1. The method of determining the concentration of β-adrenergic blocking drug and any active metabolites thereof in a body fluid containing same comprising (a) mixing together β-adrenergic receptor material, radioactive β-adrenergic receptor binder and body fluid, and measuring the amount of the radioactive β-adrenergic receptor binder on the β-adrenergic receptor material and (b) mixing together a concentration of a standard amount of non-radioactive β-adrenergic receptor binder, β-adrenergic receptor material and radioactive β-adrenergic receptor binder and measuring the amount of radioactive β-adrenergic receptor binder on the β-adrenergic receptor material.

2. The method of claim 1 in which the material, binder, and body fluid are permitted to remain together a time sufficient to produce sufficient binding of the binder and drug and any active metabolites thereof in the body fluid to said receptor material prior to making the measurement.

3. The method of claim 1 in which the materials, binder and body fluid are combined in the presence of sufficient buffer to produce a pH of about 6 to 9.

4. The method of claim 1 in which the receptor material is brain tissue, and the radioactive portion of the binder comprises $^3H$ or radioactive iodine.

5. The method of claim 1 in which iodine is $^{125}I$ or $^{131}I$.

6. The method of measuring the concentration of β-adrenergic drug and any active metabolites thereof in blood plasma or blood serum containing same which comprises (a) mixing together blood plasma or blood serum with radioactive β-adrenergic receptor binder and β-adrenergic receptor material and measuring the amount of the radioactive β-adrenergic receptor binder on the β-adreneric receptor material and (b) mixing together a concentration of a standard amount of non-radioactive β-adrenergic receptor binder, β-adreneric receptor material and the same radioactive β-adrenergic receptor binder as in (a) and measuring the amount of radioactive β-adrenergic receptor binder on the β-adrenergic receptor material.

7. The method of claim 6 in which measuring of the amount of radioactive-adrenergic receptor binder on the β-adrenergic receptor material is determined in a gamma detector or scintillation counter based upon the nature of the radioactive portion of the radioactive binder.

8. The method of claim 7 in which the concentration of drug and active metabolite is determined by reference to a standard curve representing percent inhibition of radioactive β-adrenergic receptor binder vs. non-radioactive β-adrenergic receptor binder.

9. The method of claim 1 in which the receptor material is brain tissue.

10. As a mercantile unit, a kit of at least one container of radioactive β-adrenergic receptor binder, β-adrenergic receptor material and standard non-radioactive β-adrenergic receptor binder.

11. The kit of claim 10 in which the radioactive β-adrenergic receptor binder is selected from the group consisting of radioactive labelled
propranolol
practalol
pindalol
alprenolol
sotalol
butoxamine.

12. The method of claim 7 in which unbound drug, unbound radioactive binder and plasma or serum are removed as part of determining the percent inhibition of binding.

13. The method of claim 1 in which the body fluid is blood plasma or blood serum.

14. The method of claim 1 in which the concentration of body fluid in the mixture containing same is less than about 10%.

15. The method of claim 14 in which the amount of body fluid in the mixture containing same is greater than one microliter.

16. The method of claim 1 in which radioactive β-adrenergic receptor binder is selected from the group consisting of radioactive labelled
propranolol
practalol
pindalol
alprenolol
sotalol
butoxamine.

17. The method of claim 16 in which the radioactive receptor binder is radioactive labelled propranolol.

18. The method of claim 6 in which the receptor material is brain tissue.

19. The kit of claim 11 in which said standard binder is selected from the group consisting of,
propranolol
practalol
pindalol
alprenolol
sotalol
butoxamine.

20. The method of claim 1 in which measuring of the amount of radioactive β-adrenergic receptor binder on the β-adrenergic receptor material is determined in a gamma detector or scintillation counter based upon the nature of the radioactive portion of the radioactive binder.

21. The method of claim 1 in which the concentration of drug and metabolite in the blood is determined by reference to a standard curve representing percent inhibtion of radioactive β-adrenergic receptor binder vs. non-radioactive β-adrenergic receptor binder.

22. The method of claim 1 in which (b) is repeated a sufficient number of times while varying concentration of the non-radioactive binder to provide information for generating a standard curve.

23. The method of claim 6 in which (b) is repeated a sufficient number of times while varying concentration of the non-radioactive binder to provide information for generating a standard curve.

24. The method of claim 22 in which the radioactive binder is the same in (a) and (b).

* * * * *